United States Patent [19]
Audousset

[11] Patent Number: 6,004,356
[45] Date of Patent: Dec. 21, 1999

[54] COMPOSITIONS AND PROCESSES FOR THE OXIDATION DYEING OF KERATIN FIBERS WITH OXIDATION BASES, A META-AMINOPHENOL, AND Y-HYROXYINDOLINE

[75] Inventor: Marie-Pascale Audousset, Asnières, France

[73] Assignee: L'Oreal, Paris, France

[21] Appl. No.: 08/981,790

[22] PCT Filed: Sep. 20, 1996

[86] PCT No.: PCT/FR96/01473

§ 371 Date: Dec. 30, 1997

§ 102(e) Date: Dec. 30, 1997

[87] PCT Pub. No.: WO97/11674

PCT Pub. Date: Apr. 3, 1997

[30] Foreign Application Priority Data

Sep. 25, 1995 [FR] France .................................. 95 11224

[51] Int. Cl.⁶ ..................................................... A61K 7/13
[52] U.S. Cl. .......................... 8/412; 8/409; 8/416; 8/421; 8/423
[58] Field of Search ................................ 8/406, 408, 409, 8/412, 416, 421, 423

[56] References Cited

U.S. PATENT DOCUMENTS

| | | | |
|---|---|---|---|
| 3,649,160 | 3/1972 | Kalopissis et al. | 8/409 |
| 4,013,404 | 3/1977 | Parent et al. | 8/423 |
| 5,073,173 | 12/1991 | Pan et al. | 8/412 |
| 5,609,649 | 3/1997 | Junino et al. | 8/409 |
| 5,611,817 | 3/1997 | Moeller et al. | 8/423 |
| 5,683,474 | 11/1997 | Cotteret et al. | 8/409 |
| 5,743,919 | 4/1998 | Moeller et al. | 8/423 |

FOREIGN PATENT DOCUMENTS

| | | |
|---|---|---|
| 0 428 441 | 5/1991 | European Pat. Off. . |
| 0 465 339 | 1/1992 | European Pat. Off. . |
| 0 465 340 | 1/1992 | European Pat. Off. . |
| 30 31 709 | 4/1982 | Germany . |

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratin fibers, in particular human keratin fibers such as the hair, comprising at least one suitably selected oxidation base, at least one meta-aminophenol as first coupler and 4-hydroxyindoline and/or at least one of the addition salts thereof with an acid as second coupler, and dyeing processes using this composition with an oxidizing agent.

31 Claims, No Drawings

COMPOSITIONS AND PROCESSES FOR THE OXIDATION DYEING OF KERATIN FIBERS WITH OXIDATION BASES, A META-AMINOPHENOL, AND Y-HYROXYINDOLINE

The present invention relates to a composition for the oxidation dyeing of keratin fibres, in particular human keratin fibres such as the hair, comprising at least one suitably selected oxidation base, at least one meta-aminophenol as first coupler and 4-hydroxyindoline and/or at least one of the addition salts thereof with an acid as second coupler, as well as to the dyeing process using this composition with an oxidizing agent.

It is known to dye keratin fibres, and in particular human hair, with dye compositions containing oxidation dye precursors, in particular ortho- or para-phenylenediamines, ortho- or para-aminophenols, which are generally referred to as oxidation bases. The oxidation dye precursors, or oxidation bases, are colourless or weakly coloured compounds which, when combined with oxidizing products, may give rise to coloured compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain indole or indoline compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired intensity to be obtained and have good resistance to external agents (light, bad weather, washing, permanent-waving, perspiration and rubbing).

The dyes must also allow white hairs to be covered and, lastly, they must be as unselective as possible, that is to say that they must allow the smallest possible differences in coloration to be produced over the entire length of the same keratin fibre, which may indeed be differently sensitized (i.e. damaged) between its tip and its root.

In order to produce natural or highlighted shades, it is common to use dye compositions comprising a para-phenylenediamine derivative as oxidation base and a meta-aminophenol derivative as coupler. However, the coloration obtained with such dye compositions are not entirely satisfactory since they generally have mediocre light-fastness.

Moreover, compositions for the oxidation dyeing of keratin fibres in alkaline medium, comprising at least one oxidation base such as, for example, para-phenylenediamine or a para-phenylenediamine derivative, in combination with an indoline coupler such as, for example, 4-hydroxyindoline, have already been proposed, in particular in patent application FR 2,008,797. These compositions are not entirely satisfactory either since they lead to colorations which also have mediocre light-fastness.

Now, the Applicant has just discovered that it is possible to obtain novel dyes in acidic, neutral or alkaline medium, which are capable of generating intense colorations that offer good resistance to the various attacking factors to which the hair may be subjected and in particular to the action of light, by combining at least one suitably selected oxidation base, at least one meta-aminophenol as first coupler and 4-hydroxyindoline and/or at least one of the addition salts thereof with an acid as second coupler. This result is all the more unexpected and surprising since, as indicated above, when the two couplers are used separately in combination with the same oxidation base in accordance with the invention, they lead to colorations with poor light-fastness on hair.

This discovery forms the basis of the present invention.

A first subject of the invention is thus a composition for the oxidation dyeing of keratin fibres, and in particular human keratin fibres such as the hair, characterized in that it comprises, in a medium which is suitable for dyeing:

at least one oxidation base chosen from para-phenylenediamines and/or bis(phenyl)alkylenediamines, at least one meta-aminophenol as first coupler, at least one second coupler chosen from 4-hydroxyindoline and the addition salts thereof with an acid.

The oxidation dyeing composition in accordance with the invention makes it possible to obtain intense colorations in a variety of shades, these colorations being relatively unselective and having excellent fastness properties both to atmospheric agents such as the light and bad weather and to perspiration and the various treatments to which the hair may be subjected (shampooing, permanent waving). These properties are particularly noteworthy with regard to light.

A subject of the invention is also a process for the oxidation dyeing of keratin fibres using this composition.

Among the meta-aminophenols which can be used as first coupler in the compositions in accordance with the invention, mention may be made of the compounds corresponding to formula (I) below, and the addition salts thereof with an acid:

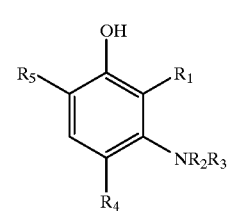

(I)

in which:

$R_1$ and $R_4$, which may be identical or different, represent a hydrogen or halogen atom or a $C_1$–$C_4$ alkyl or $C_1$–$C_4$ alkoxy radical, $R_2$ represents a hydrogen atom or a $C_1$–$C_4$ alkyl, $C_1$–$C_4$ monohydroxyalkyl, $C_2$–$C_4$ polyhydroxyalkyl, $C_1$–$C_4$ trifluoroalkyl or carbamoylmethyl radical, $R_3$ represents a hydrogen atom or a $C_1$–$C_4$ alkyl radical or alternatively forms, with $R_2$ and the nitrogen atom, a 5- or 6-membered heterocycle, $R_5$ represents a hydrogen or halogen atom or a $C_1$–$C_4$ alkyl, $C_1$–$C_4$ alkoxy, $C_1$–$C_4$ monohydroxyalkyl or $C_2$–$C_4$ polyhydroxyalkyl radical.

Among the meta-aminophenols of formula (I) above which are used as first coupler in the dye compositions in accordance with the invention, mention may be made more particularly of 3-aminophenol, 5-amino-2-methoxyphenol, 5-amino-4-chloro-2-methylphenol, 5-amino-2,4-dimethoxyphenol, 5-amino-2-β-hydroxyethyloxyphenol, 5-N-(β-hydroxyethyl)amino-4-methoxy-2-methylphenol, 5-amino-4-methoxy-2-methylphenol, 5-N-(β-hydroxypropyl)amino-2-methylphenol, 5-N-(γ-hydroxyethyl)amino-2-methylphenol, 5-amino-2- methylphenol, 3-N-(carbamoylmethyl)aminophenol, 5-N-(carbamoylmethyl)amino-2-methylphenol, 3-N,N-(dimethyl)aminophenol, 3-N,N-(diethyl)aminophenol, 3-amino-2,4-dichlorophenol, 3-amino-4,6-dichlorophenol, 5-amino-6-chloro-2-methylphenol, 2-chloro-5-N-(2',2',2'-trifluoroethyl)aminophenol, 5-amino-4-chloro-2-methylphenol and 3-N-(cyclopentyl)aminophenol, and the addition salts thereof with an acid.

Among the para-phenylenediamines which can be used as oxidation base in the compositions in accordance with the invention, mention may be made of the compounds corresponding to formula (II) below, and the addition salts thereof with an acid:

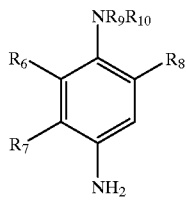

(II)

in which:

R$_6$, R$_7$ and R$_8$, which may be identical or different, represent a hydrogen or halogen atom or a C$_1$–C$_4$ alkyl, C$_1$–C$_4$ alkoxy, sulpho, carboxyl, C$_1$–C$_4$ monohydroxyalkyl or C$_2$–C$_4$ polyhydroxyalkyl radical, R$_9$ and R$_{10}$, which may be identical or different, represent a hydrogen atom, a C$_1$–C$_4$ alkyl, C$_1$–C$_4$ monohydroxyalkyl, C$_2$–C$_4$ polyhydroxyalkyl, C$_1$–C$_4$ alkoxy(C$_1$–C$_4$) alkyl, carbamyl(C$_1$–C$_4$) alkyl, C$_1$–C$_4$ mesylaminoalkyl, acetylamino(C$_1$–C$_4$) alkyl, C$_1$–C$_4$ ureidoalkyl, carb(C$_1$–C$_4$) alkoxyamino(C$_1$–C$_4$)alkyl, C$_1$–C$_4$ sulphoalkyl, piperidino (C$_1$–C$_4$) alkyl, morpholino (C$_1$–C$_4$)alkyl or phenyl radical or a phenyl radical substituted in the para position with an amino group, or alternatively R$_9$ and R$_{10}$ form, together with the nitrogen atom to which they are attached, a piperidino or morpholino heterocycle;

it being understood that if R$_9$ and R$_{10}$ do not simultaneously represent a hydrogen atom, then at least one of the radicals R$_6$ and R$_8$ must represent a hydrogen atom.

Among the C$_1$–C$_4$ alkyl and C$_1$–C$_4$ alkoxy radicals of formulae (I) and (II) above, mention may be made in particular of the methyl, ethyl, propyl, methyloxy and ethyloxy radicals.

Among the para-phenylenediamines of formula (II) above which are used as oxidation base in the dye compositions in accordance with the invention, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N,N-(ethyl, carbamylmethyl)aniline, 4-amino-3-methyl-N,N-(ethyl, carbamylmethyl)aniline, 4-amino-N,N-(ethyl, β-piperidinoethyl)aniline, 4-amino-3-methyl-N,N-(ethyl, β-piperidinoethyl)aniline, 4-amino-N,N-(ethyl, β-morpholinoethyl)aniline, 4-amino-3-methyl-N,N-(ethyl, β-morpholinoethyl)aniline, 4-amino-N,N-(ethyl, β-acetylaminoethyl)aniline, 4-amino-N-(β-methoxyethyl) aniline, 4-amino-3-methyl-N,N-(ethyl, β-acetylaminoethyl) aniline, 4-amino-N,N-(ethyl, β-mesylaminoethyl)aniline, 4-amino-3-methyl-N,N-(ethyl, β-mesylaminoethyl)aniline, 4-amino-N,N-(ethyl, β-sulphoethyl)aniline, 4-amino-3-methyl-N,N-(ethyl, β-sulphoethyl)-aniline, N-[(4'-amino) phenyl]morpholine, N-[(4'-amino)phenyl]piperidine, 2-β-hydroxyethyl-para-phenylenediamine, 2-fluoro-para-phenylenediamine, 2-carboxy-para-phenylenediamine, 2-sulpho-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts thereof with an acid.

Among the para-phenylenediamines of formula (II) above which are used as oxidation base in the dye compositions in accordance with the invention, para-phenylenediamine, para-toluylenediamine, 2,6-dimethyl-para-phenylenediamine, 2-β-hydroxyethyl-para-phenylenediamine, 2-isopropyl-para-phenylenediamine, N-(β-hydroxypropyl)-para-phenylenediamine, N,N-bis-(β-hydroxyethyl)-para-phenylenediamine and 4-amino-N-(β-methoxyethyl)aniline, and the addition salts thereof with an acid, are more particularly preferred.

Among the bis(phenyl)alkylenediamines which can be used as oxidation base in the dye compositions in accordance with the invention, mention may be made more particularly of the compounds corresponding to formula (III) below, and the addition salts thereof with an acid:

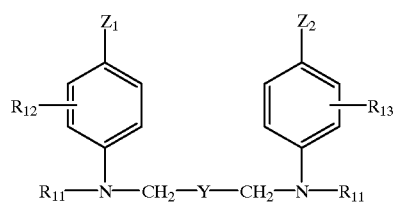

(III)

in which:

Z$_1$ and Z$_2$, which may be identical or different, represent a hydroxy radical or a radical NHR$_{14}$ in which R$_{14}$ represents a hydrogen atom or a C$_1$–C$_4$ alkyl radical, R$_{11}$ represents a hydrogen atom or a C$_1$–C$_4$ alkyl, C$_1$–C$_4$ monohydroxyalkyl or C$_2$–C$_4$ polyhydroxyalkyl radical or a C$_1$–C$_4$ aminoalkyl radical in which the amino residue may be substituted, R$_{12}$ and R$_{13}$, which may be identical or different, represent a hydrogen or halogen atom or a C$_1$–C$_4$ alkyl radical, Y represents a radical taken from the group consisting of the following radicals: —(CH$_2$)$_n$—; —(CH$_2$)$_m$—O—(CH$_2$)$_m$—; —(CH$_2$)$_m$CHOH—(CH$_2$)$_m$— and

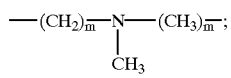

in which n is an integer between 0 and 8 inclusive and m is an integer between 0 and 4 inclusive.

Among the $C_1$–$C_4$ alkyl radicals of formula (III) above, mention may be made in particular of the methyl, ethyl and propyl radicals.

Among the bis(phenyl)alkylenediamines of formula (III) above which are used as oxidation base in the dye compositions in accordance with the invention, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis-(4-aminophenyl)tetramethylenediamine, N,N'-bis-(β-hydroxyethyl)-N,N'-bis(4-aminophenyl) tetramethylenediamine, N,N'-bis(4-methylaminophenyl) tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol is particularly preferred.

The addition salts with an acid which can be used in the context of the dye compositions of the invention are chosen in particular from the hydrochlorides, hydrobromides, sulphates and tartrates.

The oxidation base(s) in accordance with the invention, that is to say the para-phenylenediamine(s) and/or the bis (phenyl)alkylenediamine(s), preferably represent from 0.0005 to 12% by weight approximately relative to the total weight of the dye composition, and even more preferably from 0.005 to 6% by weight approximately relative to this weight.

The meta-aminophenol(s) of formula (I) which are used as first coupler in the dye compositions in accordance with the invention preferably represent from 0.0001 to 10% by weight approximately relative to the total weight of the dye composition and even more preferably from 0.005 to 5% by weight approximately relative to this weight.

The 4-hydroxyindoline and/or the addition salt(s) thereof with an acid which are used as second coupler in the dye compositions in accordance with the invention preferably represent from 0.0001 to 10% by weight approximately relative to the total weight of the dye composition and even more preferably from 0.005 to 5% by weight approximately relative to this weight.

The medium which is suitable for dyeing (or the support) generally consists of water or of a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably of between 1 and 40% by weight approximately relative to the total weight of the dye composition, and even more preferably of between 5 and 30% by weight approximately.

The pH of the dye composition in accordance with the invention is generally between 3 and 12. It may be adjusted to the desired value using acidifying or basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide or potassium hydroxide and the compounds of formula (IV) below:

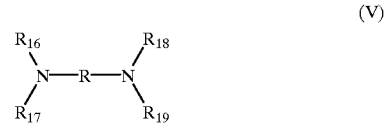

in which R is a propylene residue optionally substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

In addition to the dyes defined above, the dye composition in accordance with the invention can also contain other oxidation bases and/or other couplers and/or direct dyes, in particular in order to modify the shades or to enrich them with highlights.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to select the optional complementary compound(s) mentioned above such that the advantageous properties intrinsically associated with the ternary combination in accordance with the invention are not, or are not substantially, adversely affected by the addition or additions envisaged.

The dye composition according to the invention may be in various forms, such as in the form of liquids, creams, gels or any other form which is suitable for dyeing keratin fibres, and in particular human hair.

A subject of the invention is also a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition only at the time of use, or which is present in an oxidizing composition that is applied simultaneously or sequentially in a separate manner. According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably varies approximately between 3 and 12 and even more preferably between 5 and 11. It is adjusted to the desired value using acidifying or basifying agents usually used in the dyeing of keratin fibres and as are defined above.

The oxidizing composition as defined above may also include various adjuvants used conventionally in compositions for dyeing the hair and as are defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913 in the name of the Applicant.

The examples which follow are intended to illustrate the invention without, however, limiting the scope thereof.

EXAMPLES

Dye compositions 1 to 3 below were prepared:

| COMPOSITION | 1(*) | 2(*) | 3(**) |
|---|---|---|---|
| Para-phenylenediamine (in moles) | $3 \times 10^{-3}$ | $3 \times 10^{-3}$ | $3 \times 10^{-3}$ |
| 3-Aminophenol (in moles) | $3 \times 10^{-3}$ | — | $1.5 \times 10^{-3}$ |
| 4-Hydroxyindoline (in moles) | — | $3 \times 10^{-3}$ | $1.5 \times 10^{-3}$ |
| Common dye support | (*) | (*) | (***) |
| Demineralized water qs | 100 g | 100 g | 100 g |

(*): dye composition not forming part of the invention
(**): dye compositon in accordance with the invention
(***): common dye support:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen 012 by the company Akzo | 7.0 g |
| Diethylaminopropyl laurylamino-succinamate, sodium salt, containing 55% A.M. | 3.0 g A.M. |
| Oleyl alcohol | 5.0 g |
| Oleic acid diethanolamide | 12.0 g |
| Propylene glyco | 3.5 g |
| Ethyl alcohol | 7.0 g |
| Dipropylene glycol | 0.5 g |
| Propylene glycol monomethyl ether | 9.0 g |
| Sodium metabisulfite as an aqueous solution containing 35% A.M. | 0.455 g A.M. |
| Ammonium acetate | 0.8 g |
| Antioxidant, sequestering agent | q.s. |
| Fragrance, preserving agent | q.s. |
| Aqueous axnmonia containing 20% $NH_3$ | 10.0 g |

At the time of use, each dye composition 1 to 3 was mixed with an equal weight amount of 20-volumes aqueous hydrogen peroxide solution (6% by weight).

Each resulting mixture was applied for 30 minutes to locks of natural grey hair containing 90% white hairs. The locks of hair were then rinsed, washed with a standard shampoo and then dried.

The colour of the locks was then evaluated in the Munsell system using a Minolta CM 2002 calorimeter.

The locks of hair thus dyed then underwent a light-fastness test. The machine used to carry out the light-fastness test was a Hanau Suntest machine equipped with a xenon lamp allowing the passage of UV rays over a wavelength range of between 300 and 830 nm.

The locks were attached to a cardboard support which was introduced into the machine and irradiated for 18 hours, which corresponds to about three weeks of exposure to natural light.

The xenon lamp was cooled, during the test, using an air flow of about 60 $m^3$/hour. A second air flow of about 60 $m^3$/hour also cooled the locks.

The temperature of the locks was about 45° C.

The light intensity falling on the locks was about 150 klx.

The intensity of the irradiation was about 830 $W/m^2$.

The colour of the locks after the test was again measured in the Munsell system using a Minolta CM 2002 colorimeter.

The difference in colour of each lock before and after the light-fastness test reflects the degradation in coloration due to the action of light, and was calculated by applying the Nickerson formula: $\Delta E = 0.4\ Co\Delta H + 6\Delta V + 3\Delta C$, as described, for example, in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in absolute value of the parameters H, V and C, and Co represents the purity of the lock against which it is desired to evaluate the difference in colour (purity of the lock before the test).

The results are given in Table II below:

| Composition Example | Colour before the test | Colour after the test | Degradation of the colour | | | |
|---|---|---|---|---|---|---|
| | | | $\Delta H$ | $\Delta V$ | $\Delta C$ | $\Delta E$ |
| 1(1) | 10RP2.4/1.4 | 5.2R2.7/1.2 | 5.2 | 0.3 | 0.2 | 5.3 |
| 2(2) | 4.2YR2.7/1.4 | 5.6YR3.3/1.5 | 1.4 | 0.6 | 0.1 | 4.7 |
| 3(3) | 6.9R2.7/1.4 | 0.4YR2.8/1.3 | 3.5 | 0.1 | 0.1 | 2.9 |

These results show clearly that the dye composition of Example 3 in accordance with the invention, that is to say the composition comprising an oxidation base (para-phenylenediamine), in combination with meta-aminophenol as first coupler and 4-hydroxyindoline as second coupler, leads to a coloration which has markedly better light-fastness than the colorations obtained with the comparative dye compositions of Examples 1 and 2 (which do not form part of the invention since they contain only one of the two couplers).

I claim:

1. A composition for the oxidation dyeing of keratin fibers comprising, in a medium suitable for dyeing:
   at least one oxidation base which is a para-phenylenediamine, a bis(phenyl) alkylenediamine or an acid addition salt thereof, at least one first coupler which is a meta-aminophenol or an acid addition salt thereof, and at least one second coupler which is 4-hydroxyindoline or an acid addition salt thereof, wherein said at least one oxidation base and said at least one first and second couplers are present in amounts effective to oxidatively dye said keratin fibers.

2. A composition according to claim 1, wherein said keratin fibers are human hair.

3. A composition according to claim 1, wherein said meta-aminophenols are selected from compounds corresponding to formula (1):

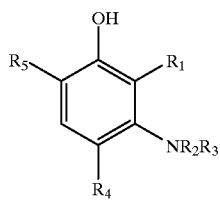

(I)

in which:

$R_1$ and $R_4$ each independently represent a hydrogen or halogen atom or a $C_1$–$C_4$ alkyl or $C_1$–$C_4$ alkoxy radical, $R_2$ represents a hydrogen atom or a $C_1$–$C_4$ alkyl, $C_1$–$C_4$ monohydroxyalkyl, $C_2$–$C_4$ polyhydroxyalkyl, $C_1$–$C_4$ trifluoroalkyl or carbamoylmethyl radical, $R_3$ represents a hydrogen atom or a $C_1$–$C_4$ alkyl radical or alternatively $R_2$ and $R_3$ form, together with the nitrogen atom to which they are attached, a 5- or 6-membered heterocycle, and $R_5$ represents a hydrogen or halogen atom or a $C_1$–$C_4$ alkyl, $C_1$–$C_4$ monohydroxyalkyl or $C_2$–$C_4$ polyhydroxyalkyl radical.

4. A composition according to claim 3, wherein said meta-aminophenol is selected from 3-aminophenol, 5-amino-2-methoxyphenol, 5-amino4-chloro-2-methyl-phenol, 5-amino-2,4-dimethoxyphenol, 5-amino-2-β-hydroxyethyloxyphenol, 5-N-(β-hydroxyethyl)amino-4-methoxy-2-methylphenol, 5-amino-4-methoxy-2-methylphenol, 5-N-(γ-hydroxypropyl)amino-2-methylphenol, 5-N-(β-hydroxyethyl)amino-2-methylphenol, 5-amino-2-methylphenol, 3-N-(carbamoylmethyl)-aminophenol, 5-N-(carbamoylmethyl)amino-2-methylphenol, 3-N, N-(dimethyl)aminophenol, 3-N,N-(diethyl)aminophenol, 3-amino-2,4-dichlorophenol, 3-amino-4,6-dichlorophenol, 5-amino-6-chloro-2-methylphenol, 2-chloro-5-N-(2',2',2'-trifluoroethyl) aminophenol, 5-amino-4-chloro-2-methylphenol or 3-N-(cyclopentyl)-aminophenol.

5. A composition according to claim 1, wherein said para-phenylenediamines are selected from compounds of formula (II):

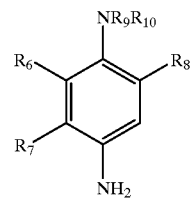

(II)

in which:

$R_6$, $R_7$ and $R_8$ each independently represent a hydrogen or halogen atom or a $C_1$–$C_4$ alkyl, $C_1$–$C_4$ alkoxy, sulpho, carboxyl, $C_1$–$C_4$ monohydroxyalkyl or $C_2$–$C_4$ polyhydroxyalkyl radical, $R_9$ and $R_{10}$ each independently represent a hydrogen atom, a $C_1$–$C_4$ alkyl, $C_1$–$C_4$ monohydroxyalkyl, $C_2$–$C_4$ polyhydroxyalkyl, $C_1$–$C_4$ alkoxy($C_1$–$C_4$)alkyl, carbamyl($C_1$–$C_4$)alkyl, $C_1$–$C_4$ mesylaminoalkyl, acetylamino($C_1$–$C_4$)alkyl, $C_1$–$C_4$ ureidoalkyl, carb ($C_1$–$C_4$)alkoxyamino($C_1$–$C_4$)alkyl, Cl-$C_4$ sulphoalkyl, piperidino($C_1$–$C_4$)alkyl, morpholino($C_1$–$C_4$)alkyl or phenyl radical or a phenyl radical substituted in the para position with an amino group, or alternatively $R_9$ and $R_{10}$ form, together with the nitrogen atom to which they are attached, a piperidino or morpholino heterocycle;

wherein if $R_9$ and $R_{10}$ do not simultaneously represent a hydrogen atom, then at least one of the radicals $R_8$ and $R_6$ must represent a hydrogen atom.

6. A composition according to claim 5, wherein said para-phenylenediamines are selected from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl) aniline, 4-amino-N,N-(ethyl, carbamylmethyl)aniline, 4-amino-3-methyl-N,N-(ethyl, carbamylmethyl)aniline, 4-amino-N,N-(ethyl, β-piperidinoethyl)aniline, 4-amino-3-methyl-N,N-(ethyl, β-piperidinoethyl)aniline, 4-amino-N, N-(ethyl, β-morpholinoethyl)aniline, 4-amino-3-methyl-N, N-(ethyl, β-morpholinoethyl)aniline, 4-amino-N,N-(ethyl, β-acetylaminoethyl)aniline, 4-amino-N-(β-methoxyethyl)-aniline, 4-amino-3-methyl-N,N-(ethyl, β-acetylamino-ethyl)aniline, 4-amino-N,N-(ethyl, β-mesylaminoethyl)-aniline, 4-amino-3-methyl-N,N-(ethyl, β-mesylamino-ethyl)aniline, 4-amino-N,N-(ethyl, β-sulphoethyl)-aniline, 4-amino-3-methyl-N,N-(ethyl, β-sulphoethyl)-aniline, N-[(4'-amino)phenyl]morpholine, N-[(4'-amino)-phenyl] piperidine, 2-β-hydroxyethyl-para-phenylene-diamine, 2-fluoro-para-phenylenediamine, 2-carboxy-para-phenylenediamine, 2-sulpho-para-phenylenediamine, 2-isopropyl-para-phenylenediamine, N-(β-hydroxypropyl)-para-phenylenediamine, 2-hydroxymethyl-para-phenylene-diamine, N,N-dimethyl-β-methyl-para-phenylenediamine, N,N-(ethyl, β-hydroxyethyl)-para-phenylenediamine, N-(β, γ-dihydroxypropyl)-para-phenylenediamine, N-(4'- aminophenyl)-para-phenylenediamine, N-phenyl-para-phenylenediamine or 2-β-hydroxyethyloxy-para-phenylenediamine.

7. A composition according to claim 6, wherein said para-phenylenediamine is selected from para-phenylenediamine, para-toluylenediamine, 2,6-dimethyl-para-phenylenediamine, 2-β-hydroxyethyl-para-phenylenediamine, 2-isopropyl-para-phenylenediamine, N-(β-hydroxypropyl)-para-phenylenediamine, N,N-bis-(β-hydroxyethyl)-para-phenylenediamine or 4-amino-N-(β-methoxyethyl)aniline.

8. A composition according to claim 1, wherein said bis(phenyl)alkylenediamines are selected from compounds of formula (III):

$$\text{(III)}$$

in which:
- $Z_1$ and $Z_2$ each independently represent a hydroxyl radical or a radical $NHR_{14}$ in which $R_{14}$ represents a hydrogen atom or a $C_1$–$C_4$ alkyl radical,
- $R_{11}$ represents a hydrogen atom or a $C_1$–$C_4$ alkyl, $C_1$–$C_{14}$ monohydroxyalkyl or $C_2$–$C_6$ polyhydroxyalkyl radical or a $C_1$–$C_4$ aminoalkyl radical in which the amino residue may be substituted,
- $R_{12}$ and $R_{13}$ each independently represent a hydrogen or halogen atom or a $C_1$–$C_4$ alkyl radical,
- Y represents one of the following radicals:

$$-(CH_2)_{\overline{n}}-; \quad -(CH_2)_{\overline{m}}-O-(CH_2)_{\overline{m}}-;$$
$$-(CH_2)_{\overline{m}}-CHOH-(CH_2)_m \text{ or } -(CH_2)_{\overline{m}}-N-(CH_2)_{\overline{m}}-;$$
$$\qquad\qquad\qquad\qquad\qquad\qquad\qquad\qquad |$$
$$\qquad\qquad\qquad\qquad\qquad\qquad\qquad\qquad CH_3$$

in which:
- n is an integer ranging from 0 to 8, and
- m is an integer ranging from 0 to 4.

9. A composition according to claim 8, wherein said bis(phenyl)alkylenediamine is selected from N,N'-bis(β-hydroxy-ethyl)-N,N'-bis(4'-aminophenyl)-1,3-diaminopropanol, N,N'-bis(β-hydroxyethyl)-N,N'-bis(4'-aminophenyl)-ethylenediamine, N,N'-bis(4-aminophenyl)tetramethylenediamine, N,N'-bis-(β-hydroxyethyl)-N,N'-bis-(4-aminophenyl)tetramethylenediamine, N,N'-bis-(4-methylaminophenyl)tetramethylenediamine or N,N'-bis(ethyl)-N,N'-bis(4'-amino-3'-methylphenyl)-ethylenediamine.

10. A composition according to claim 1, wherein said at least one oxidation base is N,N'-bis(β-hydroxy-ethyl)-N,N'-bis(4'-aminophenyl)-1,3-diaminopropanol or an acid addition salt thereof.

11. A composition according to claim 1, wherein said acid addition salt is a hydrochloride, a hydrobromide, a sulphate or a tartrate.

12. A composition according to claim 1, wherein said at least one oxidation base is present in a concentration ranging from 0.0005 to 12% by weight relative to the total weight of said composition.

13. A composition according to claim 12, wherein said at least one oxidation base is present in a concentration ranging from 0.005 to 6% by weight relative to the total weight of said composition.

14. A composition according to claim 1, wherein said at least one first coupler is present in a concentration ranging from 0.0001 to 10% by weight relative to the total weight of said composition.

15. A composition according to claim 14, wherein said at least one first coupler is present in a concentration ranging from 0.005 to 5% by weight relative to the total weight of said composition.

16. A composition according to claim 1, wherein said at least one second coupler is present in a concentration ranging from 0.0001 to 10% by weight relative to the total weight of said composition.

17. A composition according to claim 16, wherein said at least one second coupler is present in a concentration ranging from 0.005 to 5% by weight relative to the total weight of said composition.

18. A composition according to claim 1, wherein said medium suitable for dyeing comprises water or a mixture of water and at least one organic solvent.

19. A composition according to claim 18, wherein said at least one organic solvent is a $C_1$–$C_4$ lower alkanol, a glycerol, a glycol ether, or an aromatic alcohol.

20. A composition according to claim 1, wherein said composition has a pH ranging from 3 to 12.

21. A composition according to claim 1, wherein said composition is in the form of a liquid, a cream, a gel, or any form suitable for dyeing keratin fibers.

22. A process for dyeing keratin fibers comprising applying an effective amount of at least one composition according to claim 1 to said keratin fibers and developing color at acidic, neutral or alkaline pH by adding an oxidizing agent.

23. A process according to claim 22, wherein said oxidizing agent either is added to said composition at or prior to the time of application to the keratin fibers, or is present in an oxidizing composition that is simultaneously or sequentially applied in a separate manner.

24. A process according to claim 22, wherein said keratin fibers are human hair.

25. A process according to claim 22, wherein said oxidizing agent is hydrogen peroxide, urea peroxide, an alkali metal bromate or a persalt.

26. A process according to claim 25, wherein said persalt is a perborate or a persulphate.

27. A process according to claim 22, wherein said oxidizing agent is hydrogen peroxide.

28. A process according to claim 22, further comprising leaving said composition on said keratin fibers for a time ranging from 3 to 50 minutes, and then rinsing said keratin fibers, washing said keratin fibers with shampoo, rinsing said keratin fibers again and drying said keratin fibers.

29. A process according to claim 28, wherein said time ranges from 5 to 30 minutes.

30. A multi-compartment device or multi-compartment dyeing kit, wherein said device comprises a first compartment containing at least one composition for the oxidation dyeing of keratin fibers according to claim 1, and a second compartment containing an oxidizing composition.

31. A composition according to claim 1, wherein said at least one oxidation base is paraphenylenediamine, said at least one first coupler is 3-aminophenol, and said at least one second coupler is 4-hydroxyindoline.

* * * * *

UNITED STATES PATENT AND TRADEMARK OFFICE
CERTIFICATE OF CORRECTION

PATENT NO.: 6,004,356
DATED: December 21, 1999
INVENTOR(S): Marie-Pascale AUDOUSSET It is certified that an error appears in the above-identified patent and that said Letters Patent is hereby corrected as shown below:

On the title page, item [54] and col. 1:

Title, line 4, change "Y-HYDROXYINDULE" to --4-HYDROXYINDOLE--.

[30] Foreign Application Priority Data: Change "95 11224" to --96 11224--.

IN THE CLAIMS:

Claim 4, col. 9, line 48, change "amino4" to --amino-4--.

Claim 5, col. 10, line 23, change "Cl" to --$C_1$--.

Claim 6, col. 10, line 34, change "phenylenediamines are" to --phenylenediamine is--; and line 64, change "β-methyl" to --3-methyl--.

Claim 8, col. 11, line 30, change "$C_{14}$" to --$C_4$--; and line 31, change "$C_6$" to --$C_4$--.

Claim 19, col. 12, line 26, after "glycerol," insert --a glycol--.

Signed and Sealed this

Eighth Day of August, 2000

Q. TODD DICKINSON

*Attest:*

*Attesting Officer*  *Director of Patents and Trademarks*